(12) United States Patent
Tamai et al.

(10) Patent No.: US 11,423,331 B2
(45) Date of Patent: Aug. 23, 2022

(54) ANALYTICAL DATA ANALYSIS METHOD AND ANALYTICAL DATA ANALYZER

(71) Applicant: SHIMADZU CORPORATION, Kyoto (JP)

(72) Inventors: Yusuke Tamai, Kyoto (JP); Shigeki Kajihara, Kyoto (JP); Shin Fujita, Kyoto (JP); Ryota Aisu, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 511 days.

(21) Appl. No.: 16/462,611

(22) PCT Filed: Jan. 19, 2017

(86) PCT No.: PCT/JP2017/001793
§ 371 (c)(1),
(2) Date: May 21, 2019

(87) PCT Pub. No.: WO2018/134952
PCT Pub. Date: Jul. 26, 2018

(65) Prior Publication Data
US 2020/0065699 A1 Feb. 27, 2020

(51) Int. Cl.
*G06N 20/00* (2019.01)
*A61B 5/00* (2006.01)
(Continued)

(52) U.S. Cl.
CPC ........... *G06N 20/00* (2019.01); *A61B 5/0033* (2013.01); *G06T 7/0012* (2013.01); *G06V 20/69* (2022.01)

(58) Field of Classification Search
CPC ...... G06N 20/00; G06N 7/005; G06N 3/0454; G06N 3/04; G06N 3/08; G06N 3/084;
(Continued)

(56) References Cited

U.S. PATENT DOCUMENTS

| 2009/0004671 A1* | 1/2009 | Yamada | C07K 14/47 435/7.1 |
| 2010/0205124 A1* | 8/2010 | Ben-Hur | G06N 20/10 706/12 |

(Continued)

FOREIGN PATENT DOCUMENTS

| CN | 1412539 A | 4/2003 |
| JP | 2006-313124 A | 11/2006 |

(Continued)

OTHER PUBLICATIONS

Kawakami et al., "Improvement in Accuracy for Bibliography Extraction from Reference Strings in Academic Papers Using a Small Amount of Training Data", Information Processing Society of Japan, Jun. 2015, vol. 8, No. 2, pp. 18-29 (total 15 pages).

(Continued)

*Primary Examiner* — Nimesh Patel
(74) *Attorney, Agent, or Firm* — Sughrue Mion, PLLC

(57) ABSTRACT

This analytical data analysis method uses machine learning of analysis result data (31) measured by an analyzer (1), and includes generating simulated data (32) in which a data variation has been added to the analysis result data (31) within a range that does not affect identification, performing the machine learning using the generated simulated data (32), and performing discrimination using a discrimination criterion (23b) obtained through the machine learning.

14 Claims, 10 Drawing Sheets

(51) Int. Cl.
  *G06T 7/00* (2017.01)
  *G06V 20/69* (2022.01)
(58) Field of Classification Search
  CPC ........ G06N 5/046; G06N 3/049; G06N 20/10;
    G06N 3/0481; G06N 3/082; G06N 3/088;
    G06T 7/0012; G06T 2207/20084; G06T
    2207/10016; G06T 7/85; G06T 17/00;
    G06T 15/02; G06T 2207/10044; G06T
    2207/20132; G06T 2207/20224; G06T
    3/4046; G06T 3/60; G06T 5/50; G06T
    7/10; G06T 7/254; G06T 7/292; G06T
    7/80; G06K 9/00127; G06K 9/482; G06K
    9/0053; G06K 9/4628; G06K 9/6215;
    G06K 9/00718; G06K 9/6256; G06K
    9/6259; G06K 9/6276; G06K 9/0063;
    G06K 9/2018; G06K 9/209; G06K
    9/6255; G06K 9/6296; A61B 5/0033;
    H01J 49/0036; H04B 17/101; H04B
    17/373; H04B 17/3912; H04B 17/3913;
    H04L 2025/03464; H04L 25/0252; H04L
    25/0254; H04L 25/03165
  See application file for complete search history.

(56) References Cited

U.S. PATENT DOCUMENTS

| 2013/0094745 | A1* | 4/2013 | Sundar | G06T 3/0068 |
| | | | | 382/132 |
| 2015/0170536 | A1* | 6/2015 | Lan | G09B 7/02 |
| | | | | 434/350 |
| 2017/0140299 | A1 | 5/2017 | Tanji | |

FOREIGN PATENT DOCUMENTS

| JP | 5200246 B2 | 6/2013 |
| JP | 2014-44110 A | 3/2014 |
| JP | 2014-178229 A | 9/2014 |
| JP | 2016-028229 A | 2/2016 |
| WO | 2014/085826 A2 | 6/2014 |

OTHER PUBLICATIONS

Communication dated Jul. 7, 2020 from Japanese Patent Office in JP Application No. 2018-562813.
Patrice Y. Simard et al., "Best Practices for Convolutional Neural Networks Applied to Visual Document Analysis", Proceedings of the Seventh International Conference on Document Analysis and Recognition (ICDAR 2003).
International Search Report of PCT/JP2017/001793 dated Mar. 14, 2017 [PCT/ISA/210].
Written Opinion of PCT/JP2017/001793 dated Mar. 14, 2017 [PCT/ISA/237].
Office Action dated May 8, 2021 in Chinese Application No. 201780084104.7.
Communication dated Aug. 17, 2020 from the European Patent Office in European Application No. 17893044.2.
Conlin A.K. et al., "Data augmentation: an alternative approach to the analysis of spectroscopic data", Chemometrics and Intelligent Laboratory Systems, vol. 44, No. 1-2, Elsevier Science Publishers B.V. Amsterdam, NL, Dec. 14, 1998, pp. 161-173 (13 pages total).
Sáiz-Abajo M.J. et al., "Ensemble methods and data augmentation by noise addition applied to the analysis of spectroscopic data", Analytica Chimica Acta, vol. 533, No. 2, Elsevier, Amsterdam, NL, Mar. 28, 2005, pp. 147-159 (13 pages total).
Isidro Cortes-Ciriano et al., "Improved Chemical Structure-Activity Modeling Through Data Augmentation", Journal of Chemical Information and Modeling, vol. 55, No. 12, Dec. 11, 2015, pp. 2682-2692 (11 pages total).
Communication dated Nov. 15, 2021 in Chinese Application No. 201780084104.7.
Office Action dated Jun. 13, 2022 issued in corresponding Chinese Patent Application No. 201780084104.7.

* cited by examiner

FIG.1
FIRST EMBODIMENT
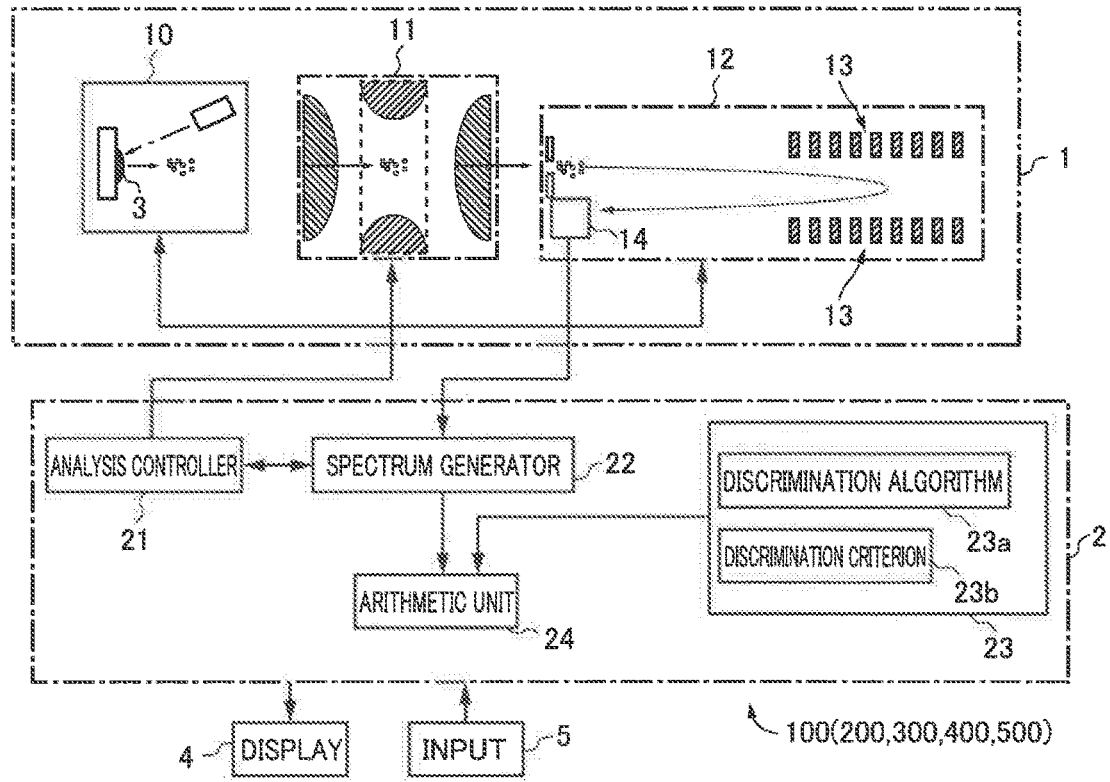
FIG.2
FIRST EMBODIMENT
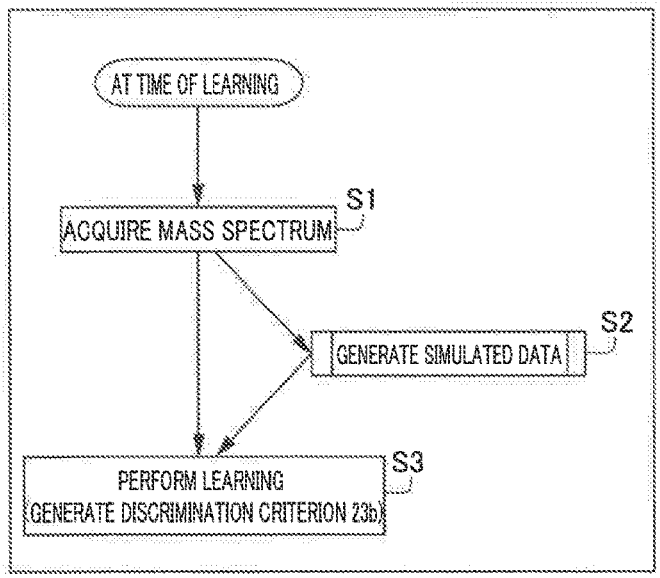
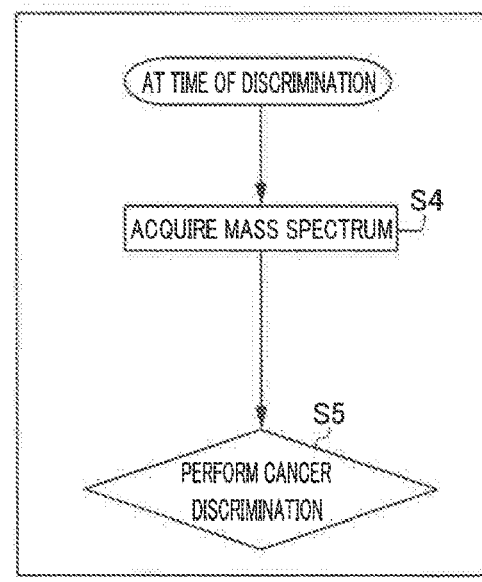

FIG.4
FIRST EMBODIMENT
(A) ANALYSIS RESULT DATA
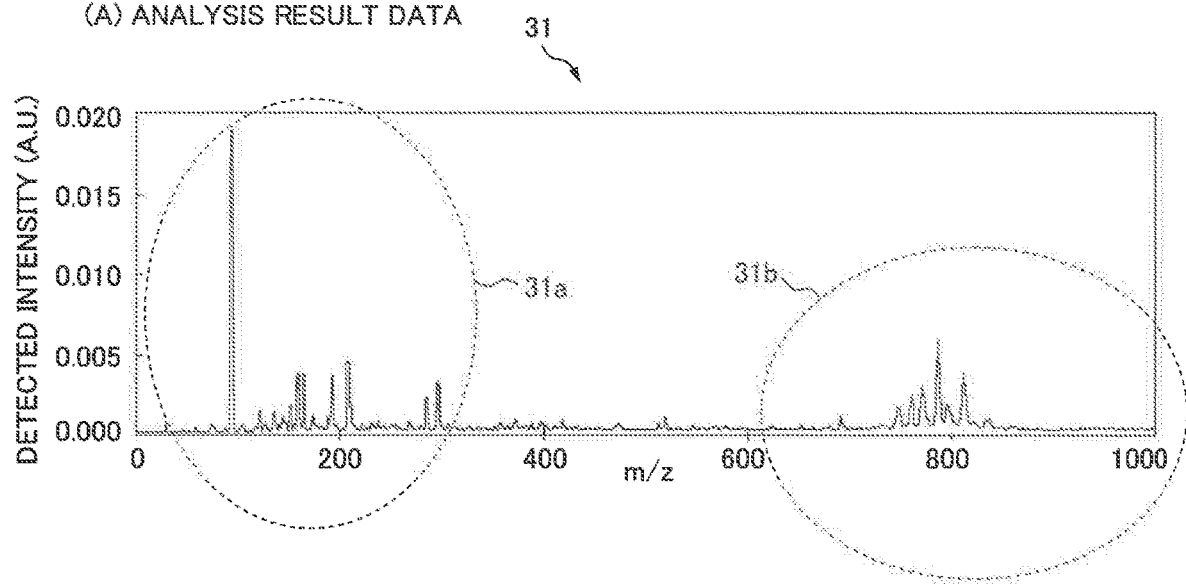
(B) SIMULATED DATA (REFLECTING INTENSITY CHANGE CAUSED BY SAMPLE)
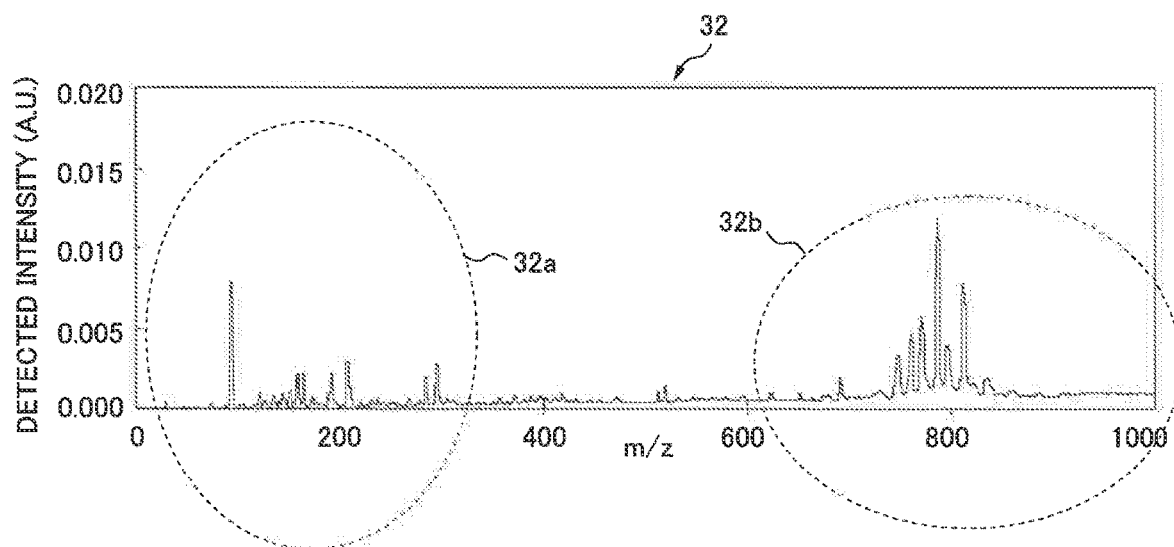

FIG.5

| NUMBER OF SPECTRA | | BEFORE ADDING | 3 TIMES | 5 TIMES |
|---|---|---|---|---|
| DISCRIMINATION AGREEMENT | 2773 | 78.51% | 81.39% | 82.51% |
| SENSITIVITY (ABNORMAL SAMPLE ACCURACY) | 1414 | 93.99% | 94.84% | 94.41% |
| SPECIFICITY (NORMAL SAMPLE ACCURACY) | 1359 | 62.40% | 67.40% | 70.13% |

FIG.6
SECOND EMBODIMENT
(A) ANALYSIS RESULT DATA
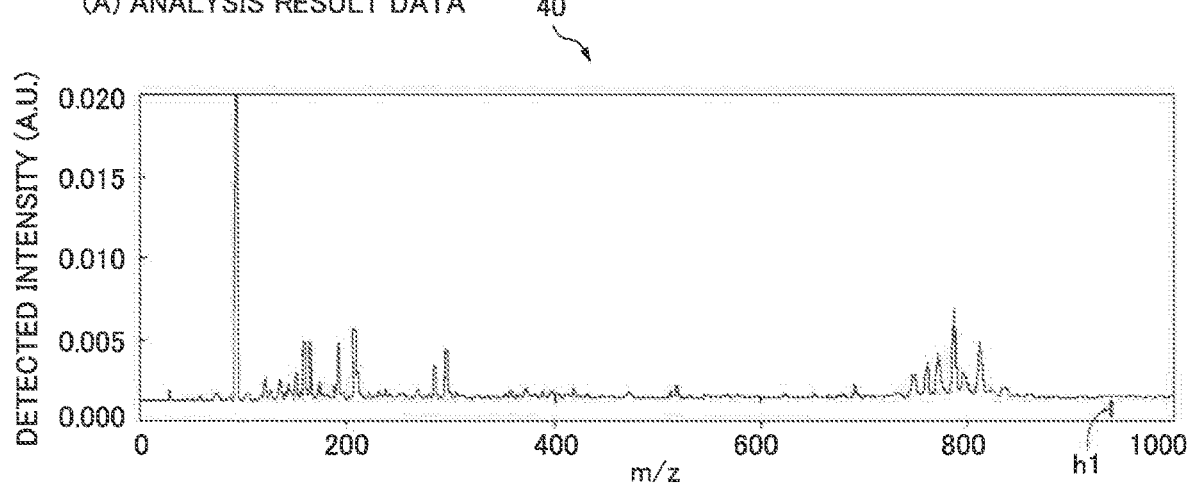
(B) SIMULATED DATA (REFLECTING VARIATION IN BASELINE)
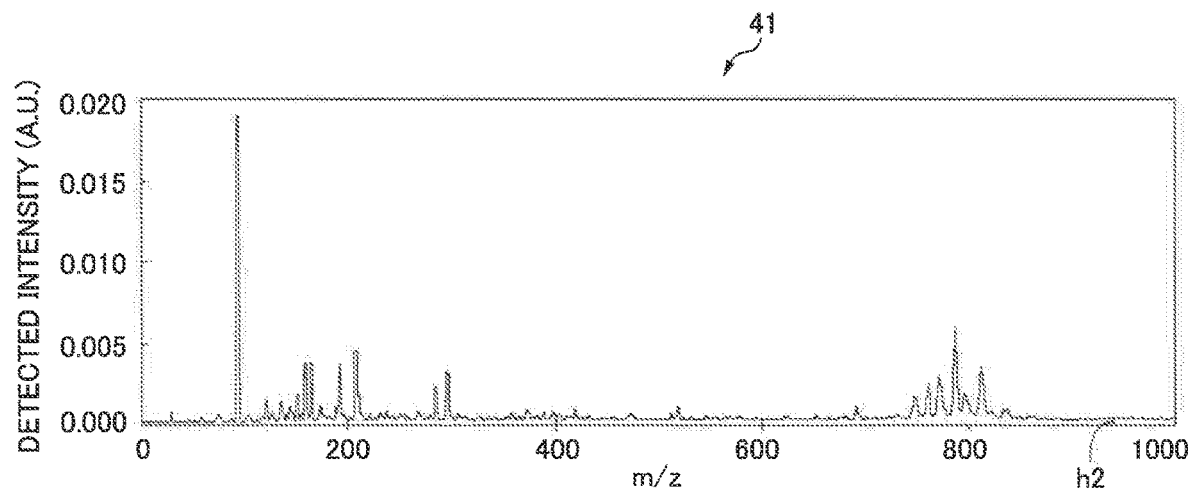

THIRD EMBODIMENT

FIG.8
THIRD EMBODIMENT
(A) ANALYSIS RESULT DATA
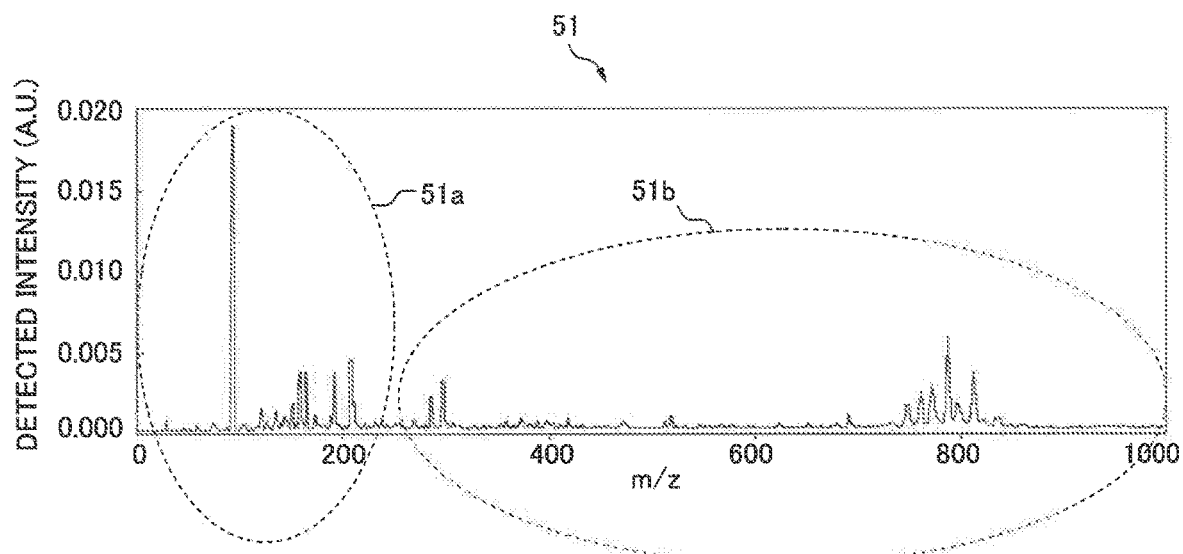
(B) SIMULATED DATA (REFLECTING DIFFERENCE IN SENSITIVITY PROFILE BETWEEN DEVICES)
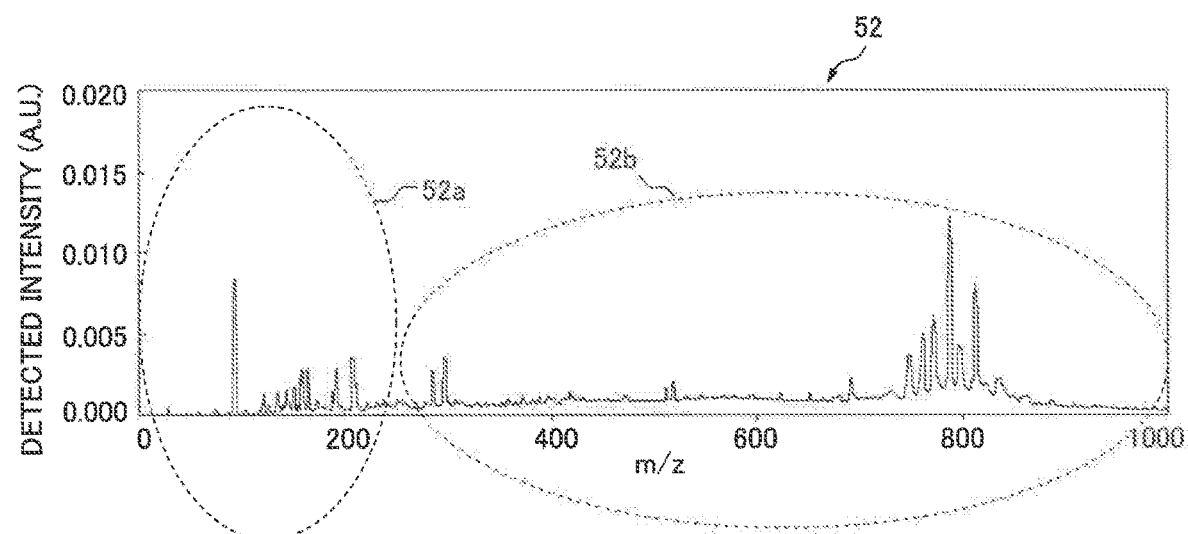

FIG.9
FOURTH EMBODIMENT
(A) ANALYSIS RESULT DATA
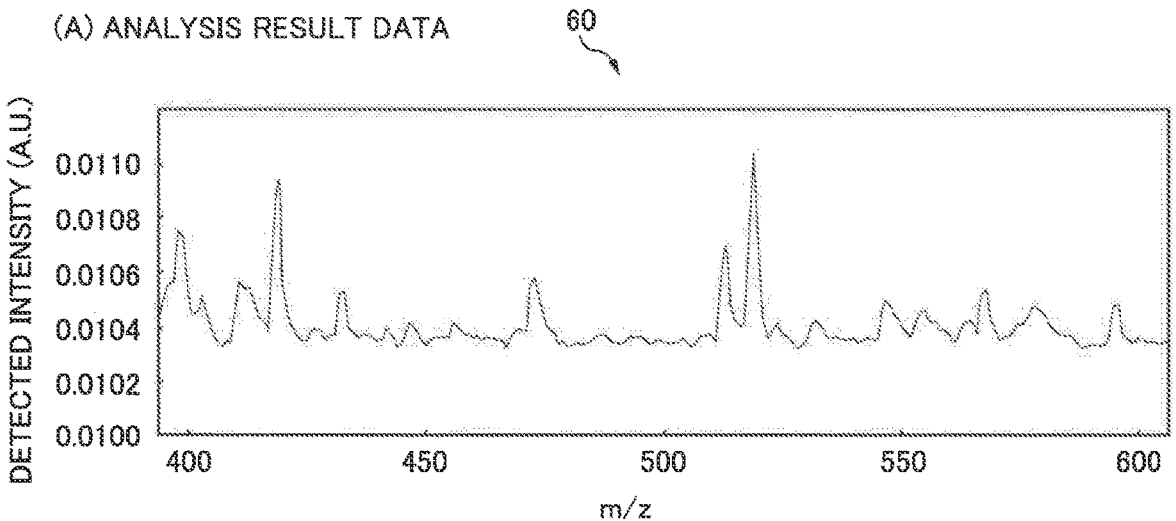
(B) SIMULATED DATA (REFLECTING RANDOM NOISE)
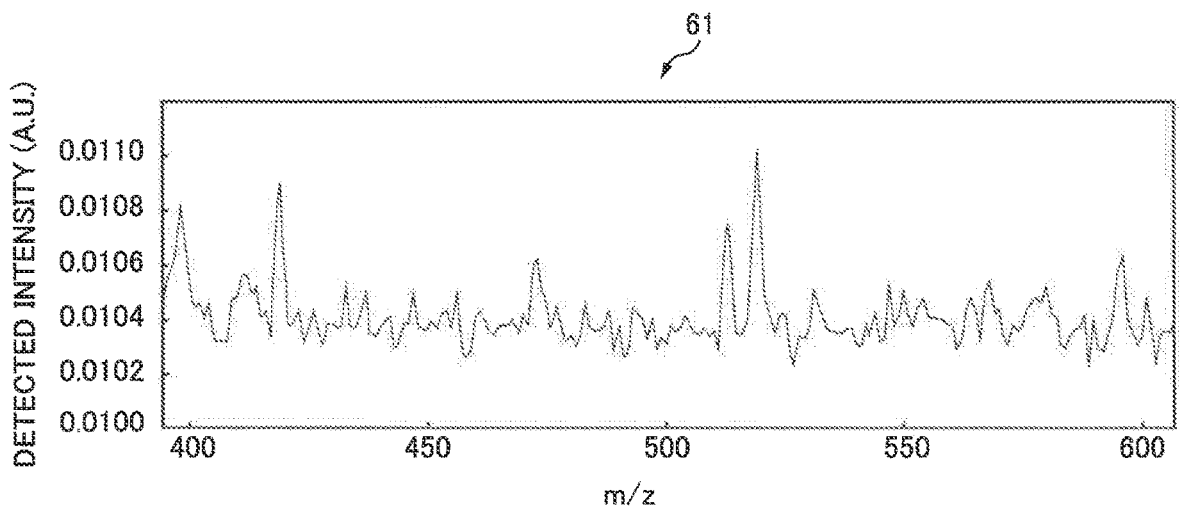

FIG.10
FIFTH EMBODIMENT
(A) ANALYSIS RESULT DATA
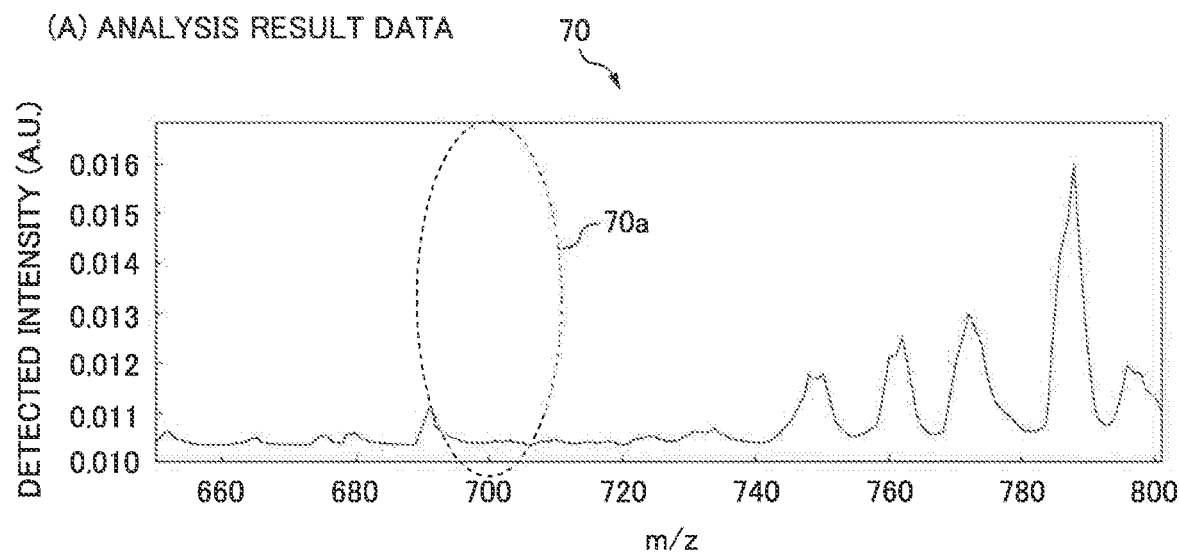
(B) SIMULATED DATA (INCLUDING PEAK OF IMPURITY)
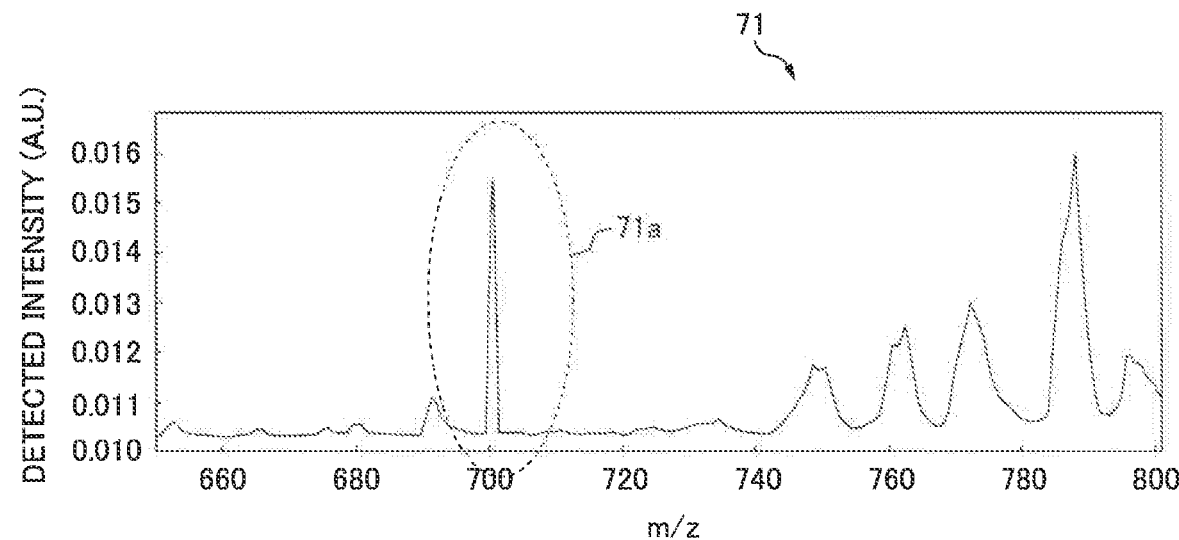

SIXTH EMBODIMENT

ANALYTICAL DATA ANALYSIS METHOD AND ANALYTICAL DATA ANALYZER

CROSS REFERENCE TO RELATED APPLICATIONS

This application is a National Stage of International Application No. PCT/JP2017/001793, filed Jan. 19, 2017.

TECHNICAL FIELD

The present invention relates to an analytical data analysis method, and more particularly, it relates to an analytical data analysis method using machine learning and an analytical data analyzer using machine learning.

BACKGROUND ART

Conventionally, an analytical data analysis method using machine learning is known. Such an analytical data analysis method is disclosed in Japanese Patent Laid-Open No. 2016-28229, for example.

Japanese Patent Laid-Open No. 2016-28229 discloses an analytical data analysis method for analyzing spectral data using machine learning. In machine learning, it is necessary to perform learning using a large amount of data (a large number of patterns). In Japanese Patent Laid-Open No. 2016-28229, spectral components are thinned out from the spectral data such that the data amount of individual learning data is reduced.

PRIOR ART

Patent Document

Patent Document 1: Japanese Patent Laid-Open No. 2016-28229

SUMMARY OF THE INVENTION

Problems to be Solved by the Invention

However, in an analytical data analysis method using machine learning such as the analytical data analysis method using machine learning disclosed in Japanese Patent Laid-Open No. 2016-28229, it is difficult to acquire a large amount of data suitable for machine learning (typical data to be discriminated). For example, it is difficult to acquire several thousands of analysis result data of a biological sample. When the amount of data used for machine learning is small, there is a problem that the accuracy of machine learning is easily reduced due to a data variation.

The present invention has been proposed in order to solve the aforementioned problems, and an object of the present invention is to provide an analytical data analysis method and an analytical data analyzer each capable of improving the accuracy of machine learning even when analytical data, in which it is difficult to acquire a large amount of typical data to be discriminated, is discriminated using machine learning.

Means for Solving the Problems

In order to attain the aforementioned object, an analytical data analysis method according to a first aspect of the present invention uses machine learning of analysis result data measured by an analyzer, and includes generating a plurality of simulated data in which a data variation has been added to a plurality of analysis result data within a range that does not affect identification, performing the machine learning using the plurality of generated simulated data, and performing discrimination using a discrimination criterion obtained through the machine learning. In the present invention, the "range that does not affect identification" is defined as a range in which the result of the discrimination is not reversed when the data variation is added.

As described above, the analytical data analysis method according to the first aspect of the present invention includes the generating of the plurality of simulated data by adding the data variation within the range that does not affect discrimination, the performing of the machine learning using the plurality of generated simulated data, and the performing of the discrimination using the discrimination criterion obtained through the machine learning. Accordingly, the plurality of simulated data in which the variation has been added within the range that does not affect identification can be generated. Consequently, the amount of data used for the machine learning can be increased, and thus the accuracy of the machine learning can be improved.

Here, in the field of image recognition, it is easy to increase the amount of data by adding a conversion to the acquired image, but in the case of scientific analysis data, it is difficult to identify a range in which the data can be varied. When data is only increased, learning is performed on training data, but there is a possibility that the discrimination accuracy may be decreased due to over-fitting, which is a state in which fit (generalization) to unknown data (data to be discriminated) cannot be established. Therefore, in the aforementioned analytical data analysis method according to the first aspect, the range that does not affect identification is preferably a range corresponding to a specific variation factor associated with measurement by the analyzer. Accordingly, variations such as data variations or biases caused by various factors associated with the measurement by the analyzer can be converted to simulated data, and learning can be performed. Consequently, a decrease in the accuracy of the machine learning caused by the variation factor associated with the measurement by the analyzer can be significantly reduced or prevented.

In this case, each of the plurality of analysis result data is preferably a spectrum obtained by the analyzer, and the specific variation factor is preferably a variation factor caused by the analyzer or a sample and generated when the spectrum is obtained by the analyzer. Accordingly, a large amount of simulated data generated by adding a variation generated in association with actual measurement to the spectrum, the distribution of which makes it difficult to evaluate the variable range, not simple numerical data can be learned. Consequently, a decrease in the accuracy of the machine learning caused by the variation factor caused by the analyser or the sample and generated in association with actual measurement can be significantly reduced or prevented.

In the aforementioned analytical data analysis method in which the range that does not affect identification is the range corresponding to the specific variation factor associated with the measurement by the analyzer, the plurality of simulated data are preferably generated by adding the data variation within a range of variation in the plurality of analysis result data caused by the specific variation factor. Accordingly, learning can be performed using the plurality of simulated data generated by adding the variation associated with the measurement by the analyzer. Consequently, a decrease in the accuracy of the machine learning caused by a plurality of variation factors associated with the measurement by the analyzer can be significantly reduced or prevented.

In this case, the analytical data analysis method preferably includes acquiring the variation in the plurality of analysis result data caused by the specific variation factor, and generating the plurality of simulated data by adding the acquired variation in the plurality of analysis result data caused by the specific variation factor. Accordingly, learning can be performed using the simulated data corresponding to the variation factor generated in association with actual measurement, and learning using simulated data in which a data variation not associated with the measurement has been added can be significantly reduced or prevented. Consequently, over-fitting can be significantly reduced or prevented, and thus a decrease in the accuracy of the machine learning can be significantly reduced or prevented.

In the aforementioned analytical data analysis method in which the data variation has been added to the plurality of analysis result data within the range of the variation caused by the specific variation factor, the generating of the plurality of simulated data preferably includes generating the plurality of simulated data by varying a value of an intensity of the spectrum according to a ratio of change of the intensity of the spectrum caused by the sample. Accordingly, learning can be performed using the simulated data corresponding to the ratio of change in the intensity of the spectrum that differs for each sample as one of the variation factors associated with the measurement. Consequently, a decrease in the accuracy of the machine learning caused by the ratio of change in the intensity of the spectrum that differs for each sample can be significantly reduced or prevented.

In the aforementioned analytical data analysis method in which the data variation has been added to the plurality of analysis result data within the range of the variation caused by the specific variation factor, the ratio of change of the intensity of the spectrum caused by the sample preferably increases or decreases at a substantially constant rate as a mass of the sample or a wavelength absorbed by the sample increases, and the plurality of simulated data are preferably generated by multiplying the value of the intensity of the spectrum by the ratio of change of the intensity. Accordingly, learning can be performed using the simulated data in which the ratio of change of the intensity of the spectrum according to the value of the mass of the sample or the value of the wavelength absorbed by the sample is reflected. Consequently, a decrease in the accuracy of the machine learning caused by the ratio of change of the intensity of the spectrum according to the value of the mass of the sample or the value of the wavelength absorbed by the sample can be significantly reduced or prevented.

In the aforementioned analytical data analysis method in which the data variation has been added to the plurality of analysis result data within the range of the variation caused by the specific variation factor, the generating of the plurality of simulated data preferably includes generating the plurality of simulated data by giving, to a baseline of the spectrum, a variation corresponding to a variation in the baseline generated at a time of measuring the plurality of analysis result data. Accordingly, learning can be performed using the simulated data corresponding to a difference in measurement environment as one of the variation factors associated with the measurement. Consequently, a decrease in the accuracy of the machine learning due to the difference in measurement environment can be significantly reduced or prevented.

In the aforementioned analytical data analysis method in which the data variation has been added to the plurality of analysis result data within the range of the variation caused by the specific variation factor, the generating of the plurality of simulated data preferably includes generating the plurality of simulated data by adding a difference in individual difference data of each of a plurality of analyzers. Accordingly, learning can be performed using the simulated data corresponding to an error of the detection sensitivity of the spectrum between the analyzers as one of the variation factors associated with the measurement. Consequently, a decrease in the accuracy of the machine learning due to the error of the detection sensitivity between the analyzers can be significantly reduced or prevented.

In the aforementioned analytical data analysis method in which the data variation has been added to the plurality of analysis result data within the range of the variation caused by the specific variation factor, the generating of the plurality of simulated data preferably includes generating the plurality of simulated data by adding a random number to the plurality of analysis result data within the range that does not affect identification. Accordingly, learning can be performed using the simulated data corresponding to the random noise as one of the variation factors associated with the measurement. Consequently, when noise is mixed at the time of measurement, a decrease in the accuracy of the machine learning can be significantly reduced or prevented.

In the aforementioned analytical data analysis method in which the data variation has been added to the plurality of analysis result data within the range of the variation caused by the specific variation factor, the generating of the plurality of simulated data preferably includes generating the plurality of simulated data by adding a peak of an impurity to the spectrum according to the impurity detected at a time of the measurement by the analyzer. Accordingly, learning can be performed using the simulated data corresponding to the mixing of impurity as one of the variation factors associated with the measurement. Consequently, a decrease in the accuracy of the machine learning can be significantly reduced or prevented when the impurity is mixed.

In the aforementioned analytical data analysis method in which the specific variation factor is the variation factor caused by the analyzer or the sample and generated when the spectrum is obtained by the analyzer, the machine learning is preferably performed, using the plurality of simulated data, on the plurality of analysis result data measured by a mass spectrometer that generates a mass spectrum as the analyzer. Accordingly, the plurality of simulated data in which the variation associated with the measurement by the mass spectrometer has been added to the obtained mass spectrum can be generated and used for the machine learning. Consequently, a decrease in the accuracy of the machine learning due to the specific factor associated with the measurement by the mass spectrometer can be significantly reduced or prevented.

In this case, the plurality of analysis result data preferably include the mass spectrum of a biological sample collected from a subject, and the performing of the discrimination preferably includes performing cancer discrimination on the plurality of analysis result data of the sample using the discrimination criterion. Accordingly, the cancer discrimination can be performed by discriminating, with the discrimination criterion generated through the machine learning, the data of the mass spectrum using the biological sample difficult to obtain in large numbers.

An analytical data analyzer according to a second aspect of the present invention includes a data input that acquires analysis result data obtained by another analyzer, a storage that stores a discrimination criterion generated through machine learning using simulated data generated by adding a data variation to the analysis result data within a range that does not affect identification, and a discrimination algorithm for the machine learning, and an arithmetic unit that discriminates the analysis result data acquired by the data input according to the discrimination algorithm using the discrimination criterion.

As described above, the analytical data analyzer according to the second aspect of the present invention includes the data input that acquires the analysis result data, the storage that stores the discrimination criterion generated through the machine learning using the simulated data generated by adding the data variation to the analysis result data within the range that does not affect identification, and the discrimination algorithm for the machine learning, and the arithmetic unit that discriminates the analysis result data acquired using the discrimination criterion. Accordingly, the plurality of simulated data in which the variation has been added within the range that does not affect identification can be generated. Consequently, the amount of data used for the machine learning can be increased, and thus the accuracy of the machine learning can be improved.

Effect of the Invention

As described above, according to the present invention, it is possible to provide the analytical data analysis method and the data analyzer each capable of improving the accuracy of machine learning even when analytical data, in which it is difficult to acquire a large amount of typical data to be discriminated, is discriminated using machine learning.

BRIEF DESCRIPTION OF THE DRAWINGS

FIG. 1 is a block diagram schematically showing an analytical data analyzer according to first to fifth embodiments of the present invention.

FIG. 2 is flowcharts showing a flow at the time of learning (A) and a flow at the time of discrimination (B) according to the first embodiment of the present invention.

FIG. 4 is spectrum diagrams showing analysis result data (A) used in the first embodiment of the present invention and simulated data (B) generated in the first embodiment of the present invention.

FIG. 5 is a table illustrating the discrimination results of the first embodiment of the present invention.

FIG. 6 is a spectrum diagram showing analysis result data (A) used in a second embodiment of the present invention and simulated data (B) generated in the second embodiment of the present invention.

FIG. 8 is a spectrum diagram showing analysis result data (A) used in a third embodiment of the present invention and simulated data (B) generated in the third embodiment of the present invention.

FIG. 9 is a spectrum diagram showing analysis result data (A) used in a fourth embodiment of the present invention and simulated data (B) generated in the fourth embodiment of the present invention.

FIG. 10 is a spectrum diagram showing analysis result data (A) used in a fifth embodiment of the present invention and simulated data (B) generated in the fifth embodiment of the present invention.

MODES FOR CARRYING OUT THE INVENTION

Figure 3:
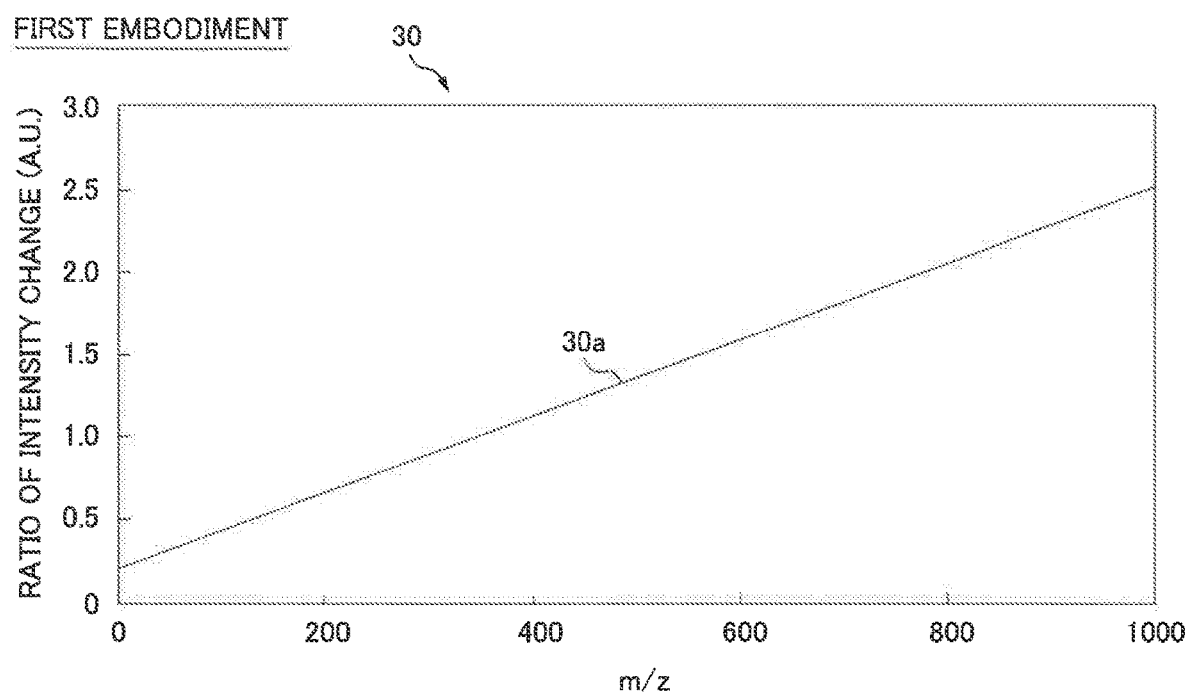
FIG. 3 is a graph showing the ratio of the intensity of a sample according to the first embodiment of the present invention.

Embodiments embodying the present invention are hereinafter described on the basis of the drawings.
[First Embodiment]
The structure of an analytical data analyzer 100 according to a first embodiment is now described with reference to FIGS. 1 to 5.

As shown in FIG. 1, the analytical data analyzer 100 includes a data processor 2. In addition, an analytical data analysis system is constructed by the analytical data analyzer 100 and an analyzer 1. The analytical data analyzer 100 also functions as a controller of the analyzer 1.

The analytical data analyzer 100 performs machine learning using a generated mass spectrum 32 (see FIG. 4B), and discriminates a sample 3 using a discrimination criterion 23b obtained as a result. The discrimination is, for example, discrimination of cancer or the like when the sample 3 is a biological sample. When the sample 3 is a non-biological sample, the discrimination is, for example, material discrimination or the like.

The analyzer 1 is a device that performs scientific analysis of the measurement sample 3. The analyzer 1 generates, for example, a spectrum as analysis result data. Although any analyzer may be used as long as the same generates a spectrum, the analyzer 1 is a mass spectrometer that generates a mass spectrum, for example. In the first embodiment, machine learning is performed on a plurality of analysis result data measured by the analyzer 1 that generates a mass spectrum as an analyzer, using a plurality of simulated data.

The analyzer 1 may be of any type, but is a matrix-assisted laser desorption ionization-quadrupole ion-trap time-of-flight mass spectrometer (MALDI-QIT-TOFMS), for example.

The analyzer 1 includes an ionizer 10, an ion trap 11, and a time-of-flight mass analyzer 12.

The analyzer 1 ionizes the sample 3 in the ionizer 10 by a MALDI method, temporarily captures generated ions by the ion trap 11, and selects ions according to the mass-to-charge ratio (m/z). The ions emitted from the ion trap 11 are folded back by an electric field generated by reflectron electrodes 13 provided in the time-of-flight mass analyzer 12 and are detected by an ion detector 14.

The data processor 2 includes an analysis controller 21, a spectrum generator 22, a storage 23, and an arithmetic unit 24. The storage 23 stores a discrimination algorithm 23a used for discrimination and the discrimination criterion 23b generated by machine learning. The discrimination criterion 23b is a parameter used for discrimination generated by machine learning. As an example of machine learning, an SVM (support vector machine) is used, for example. The discrimination is discrimination of cancer, for example.

The analysis controller 21 controls the ionizer 10, the ion trap 11, and the time-of-flight mass analyzer 12. In addition, the spectrum generator 22 generates a mass spectrum based on a value detected by the ion detector 14 and transmits data of the generated mass spectrum to the arithmetic unit 24. The arithmetic unit 24 discriminates the input mass spectrum using the discrimination algorithm 23a and the discrimination criterion 23b stored in the storage 23.

An input 5 is, for example, a keyboard, a mouse, a touch panel, etc. and is connected to the data processor 2, and an operation for starting spectrum analysis, for example, is performed via the input 5. A display 4 is, for example, a monitor such as a liquid crystal display connected to the data processor 2 and displays the discrimination results etc.

In the first embodiment, the measurement sample 3 is a biological sample. For example, the measurement sample 3 is urine or blood collected from a subject. Furthermore, in the first embodiment, the analysis result data includes the mass spectrum of the biological sample 3 collected from the subject, and in a discrimination step, discrimination of cancer on the plurality of analysis result data of the sample 3 is performed using the discrimination criterion 23b.

A flow at the time of learning and a flow at the time of discrimination according to the first embodiment are now described with reference to FIG. 2.

First, the flow of learning is described with reference to FIG. 2(A). The learning is performed before the mass spectrum of the sample 3 is discriminated by a learning device (a computer, for example) separate from the data processor 2. FIG. 2(A) is a flowchart showing the flow at the time of learning. In step S1, the mass spectrum of the sample 3 is acquired. Then, in step S2, the plurality of simulated data in which a variation factor generated due to the measurement has been added is generated. Next, in step S3, machine learning is performed using the acquired mass spectrum and the plurality of generated simulated data, and the discrimination criterion 23b is generated.

Next, the flow at the time of discrimination is described with reference to FIG. 2(B). The discrimination is performed by the arithmetic unit 24 of the data processor 2. FIG. 2(B) is a flowchart showing the flow at the time of discrimination. In step S4, the mass spectrum of the sample 3 is acquired. Next, in step S5, cancer discrimination is performed using the discrimination criterion 23b generated in step S3.

Steps of generating the simulated data according to the first embodiment of the present invention are now described with reference to FIGS. 3 and 4.

FIG. 3 is a graph 30 showing the relationship between the mass-to-charge ratio of the spectrum of the sample 3 and the ratio of change of the intensity of the obtained spectrum, in which the horizontal axis represents the mass-to-charge ratio (m/z) and the vertical axis represents the ratio of change of the intensity of the obtained spectrum. In mass spectrometry, the intensity of the obtained spectrum may differ from its actual value depending on the sample to be measured. In the first embodiment, in the mass spectrum of the sample 3, the detected intensity obtained in a range in which the mass-to-charge ratio is smaller is larger than its actual value, and the detected intensity is conversely smaller than its actual value in a range in which the mass-to-charge ratio is larger. A straight line 30a indicates the ratio of the mass spectrum of the sample 3 as compared with its actual value, and the ratio of intensity change increases at a substantially constant rate as the mass-to-charge ratio increases.

FIG. 4(A) shows the mass spectrum 31 of the analysis result data of the sample 3, and FIG. 4(B) shows the mass spectrum 32 of the simulated data generated by adding a data variation to the mass spectrum 31 within a range that does not affect identification. In addition, the expression "range that does not affect identification" indicates a range corresponding to a specific variation factor associated with the measurement by the analyzer 1, and in the first embodiment, an example is described in which the simulated data is generated by adding a variation caused by a variation factor caused by the sample 3 when the mass spectrum 31 of the sample 3 is obtained by the analyzer 1 among these variation factors. That is, the mass spectrum 32 is generated by adding the data variation within the range of variation in the mass spectrum 31 caused by the ratio of intensity change of the sample 3. The mass spectrum 31 and the mass spectrum 32 are examples of a "plurality of analysis result data" and a "plurality of simulated data" in the claims.

In the first embodiment, a step of acquiring the variation in the plurality of analysis result data caused by the specific variation factor and a step of generating the plurality of simulated data by adding the variation in the plurality of analysis result data caused by the acquired specific variation factor are included. Specifically, the mass spectrum 32, which is the simulated data, is generated by acquiring the ratio of change of the intensity of the mass spectrum 31, which is the analysis result data of the sample 3, and multiplying the mass spectrum 31 by the acquired ratio of intensity change. As shown in the graph of FIG. 3, in a mass-to-charge ratio range of 400 or less, the intensity ratio value is 1.0 or less, and thus the detected intensity of the spectrum of a region 32a of the generated mass spectrum 32 is smaller than the detected intensity of a region 31a of the spectrum 31. In addition, in a range in which the mass-to-charge ratio is more than 400, the value of the intensity ratio is more than 1.0, and thus the detected intensity of a region 32b of the generated mass spectrum 32 is larger than the detected intensity of a region 31b of the mass spectrum 31.

In the first embodiment, the plurality of simulated data in which the variation has been added within the range of the ratio on the straight line 30a shown in the graph 30 of FIG. 3 are generated, and machine learning is performed.

FIG. 5 is a diagram showing the results obtained by generating the simulated data such that the data amount of correct (cancer) data and the data amount of incorrect (non-cancer) data are respectively three and five times the analysis result data collected in advance, performing machine learning, and discriminating the sample 3 using the generated discrimination criterion 23b. The discrimination agreement and the specificity are improved in accuracy as the amount of data increases. In addition, the accuracy of the sensitivity slightly decreases when the amount of data is increased from three to five times, but this is because the sensitivity approaches its true value due to the improvement in the discrimination agreement. Here, the data amount of three times and the data amount of five times indicate the data amount in which the total of the analysis result data and the simulated data is three times the analysis result data and the data amount in which the total of the analysis result data and the simulated data is five times the analysis result data. In the present specification, the term "sensitivity" is, for example, a ratio at which cancer has been determined to be cancer in the case of cancer discrimination, and the term "specificity" is a ratio at which non-cancer has been determined to be non-cancer.

(Effects of First Embodiment)

According to the first embodiment, the following effects are achieved.

According to the first embodiment, as described above, in the analytical data analyzer 100, the spectrum generator 22 of the data processor 2 generates the mass spectrum 31 based on the ion intensity of the sample 3 detected by the ion detector 14 of the analyzer 1. The mass spectrum 31 generated by the spectrum generator 22 is transmitted to the arithmetic unit 24. The arithmetic unit 24 discriminates the input mass spectrum 31 using the discrimination algorithm 23a and the discrimination criterion 23b stored in the storage 23. Furthermore, according to the first embodiment, a step of generating the mass spectrum 32 by multiplying the mass spectrum 31 by the ratio of intensity change for each mass-to-charge ratio of the sample 3 is included. Accordingly, the simulated data (mass spectrum 32) in which the variation has been added within the range that does not affect identification can be generated. Consequently, the amount of data used for machine learning can be increased, and thus the accuracy of machine learning can be improved.

According to the first embodiment, as described above, the range that does not affect identification is the range corresponding to the specific variation factor associated with the measurement by the analyzer 1. Accordingly, data corresponding to the variation factor associated with the measurement by the analyzer 1 can be learned, and thus a decrease in the accuracy of machine learning caused by the variation factor associated with the measurement by the analyzer 1 can be significantly reduced or prevented.

According to the first embodiment, as described above, the analysis result data is the mass spectrum 31 obtained by the analyzer 1, and the specific variation factor is the variation factor caused by the sample 3 and generated when the mass spectrum 31 is obtained by the analyzer 1.

Accordingly, the mass spectrum 32 corresponding to the variation factor caused by the sample 3 at the time of obtaining the mass spectrum 31 can be learned, and thus a decrease in the accuracy of machine learning caused by the variation factor caused by the sample 3 can be significantly reduced or prevented.

According to the first embodiment, as described above, the mass spectrum 32 is generated by adding the data variation within the range of variation in the mass spectrum 31 caused by the ratio of intensity change of the sample 3. Accordingly, learning can be performed using the mass spectrum 32 generated by adding the variation associated with the measurement by the analyzer 1. Consequently, a decrease in the accuracy of machine learning caused by a plurality of variation factors associated with the measurement by the analyzer 1 can be significantly reduced or prevented.

According to the first embodiment, as described above, the step of acquiring the variation in the mass spectrum 31 caused by the ratio of intensity change of the sample 3 and the step of generating the mass spectrum 32 by adding the acquired variation in the mass spectrum 31 caused by the ratio of intensity change of the sample 3 are included. Accordingly, learning can be performed using the mass spectrum 32 corresponding to the ratio of intensity change of the sample 3 associated with the measurement, and learning using a data variation not associated with the measurement can be significantly reduced or prevented. Consequently, over-fitting can be significantly reduced or prevented, and thus a decrease in the accuracy of machine learning can be significantly reduced or prevented.

According to the first embodiment, as described above, the mass spectrum 32 is generated by varying the value of the intensity of the mass spectrum 31 according to the ratio of change of the intensity of the mass spectrum 31 caused by the sample 3 in the step of generating the simulated data. Accordingly, learning can be performed using the mass spectrum 32 corresponding to the ratio of change in the intensity of the mass spectrum 31 that differs for each sample 3. Consequently, a decrease in the accuracy of machine learning caused by the ratio of change in the intensity of the mass spectrum 31 that differs for each sample 3 can be significantly reduced or prevented.

According to the first embodiment, as described above, the ratio of change of the intensity of the mass spectrum 31 caused by the sample 3 increases at the substantially constant rate as the mass of the sample 3 increases, and the mass spectrum 32 is generated by multiplying the value of the intensity of the mass spectrum 31 by the ratio of intensity change. Accordingly, learning can be performed using the mass spectrum 32 in which the ratio of change of the intensity of the mass spectrum 31 according to the mass of the sample 3 is reflected. Consequently, a decrease in the accuracy of machine learning caused by the ratio of change of the intensity of the mass spectrum 31 according to the value of the mass of the sample 3 can be significantly reduced or prevented.

According to the first embodiment, as described above, machine learning is performed, using the mass spectrum 32, on the mass spectrum 31 measured by the analyzer 1 that generates the mass spectrum as an analyzer. Accordingly, the mass spectrum 32 in which the variation associated with the measurement by the analyzer 1 has been added to the obtained mass spectrum 31 can be generated and used for machine learning. Consequently, a decrease in the accuracy of machine learning due to the specific factor associated with the measurement by the analyzer 1 can be significantly reduced or prevented.

According to the first embodiment, as described above, the analysis result data includes the mass spectrum 31 of the biological sample 3 collected from the subject, and in the discrimination step, cancer discrimination is performed on the mass spectrum 31 of the sample 3 using the discrimination criterion 23b. Accordingly, cancer discrimination can be performed by discriminating the data of the mass spectrum 31 through machine learning. The biological sample 3 is, for example, blood or urine collected from the subject.

[Second Embodiment]

The structure of an analytical data analyzer 200 according to a second embodiment is now described with reference to FIGS. 1 and 6. In the second embodiment, an example in which simulated data is generated by adding a variation caused by a variation in a baseline of a mass spectrum of a sample 3 among specific variation factors associated with the measurement is described.

FIG. 6 shows a mass spectrum 40 of the sample 3 and a mass spectrum 41 generated by giving a variation corresponding to the variation in the baseline generated when the mass spectrum 40 is measured. The height h2 of the baseline of the mass spectrum 41 is smaller than the height h1 of the baseline of the mass spectrum 40. The mass spectrum 40 and the mass spectrum 41 are examples of a "plurality of analysis result data" and a "plurality of simulated data" in the claims.

In the analytical data analyzer 200 according to the second embodiment, in a step of generating the simulated data, the simulated data corresponding to the variation in the baseline of the mass spectrum 40 of the sample 3 is generated unlike the first embodiment in which the mass spectrum 32 corresponding to the ratio of change of the intensity of the mass spectrum 31 of the sample 3 is generated. In the second embodiment, the same structures as those of the aforementioned first embodiment are denoted by the same reference numerals, and description thereof is omitted.

As shown in FIG. 6, in the analytical data analyzer 200 according to the second embodiment, in the step of generating the simulated data, the mass spectrum 41 is generated by giving, to the baseline of the mass spectrum 40 of the sample 3, the variation corresponding to the variation in the baseline generated at the time of measuring the mass spectrum 40. Then, learning is performed using the generated mass spectrum 41, a discrimination criterion 23b is generated, and discrimination is performed using the generated discrimination criterion 23b. In the second embodiment, a plurality of simulated data are generated by lowering or raising the baseline of the mass spectrum 40 within a range of rising or falling of the baseline of the mass spectrum 40 of the sample 3, and machine learning is performed.

The remaining structures of the analytical data analyzer 200 according to the second embodiment are similar to those of the analytical data analyzer 100 according to the first embodiment.

(Effects of Second Embodiment)

According to the second embodiment, the following effects are achieved.

According to the second embodiment, as described above, the mass spectrum 41 is generated by giving, to the baseline of the mass spectrum 40 of the sample 3, the variation corresponding to the variation in the baseline generated at the time of measuring the mass spectrum 40. Accordingly, learning can be performed using the mass spectrum 41 corresponding to a difference in measurement environment. Consequently, a decrease in the accuracy of machine learning due to the difference in measurement environment can be significantly reduced or prevented.

The remaining effects of the analytical data analyzer 200 according to the second embodiment are similar to those of the analytical data analyzer 100 according to the first embodiment.

[Third Embodiment]

The structure of an analytical data analyzer 300 according to a third embodiment is now described with reference to FIGS. 1, 7, and 8. In the third embodiment, an example in which simulated data is generated by adding a variation caused by a difference in individual difference data of an analyzer 1 among specific variation factors associated with the measurement is described.

Figure 7:
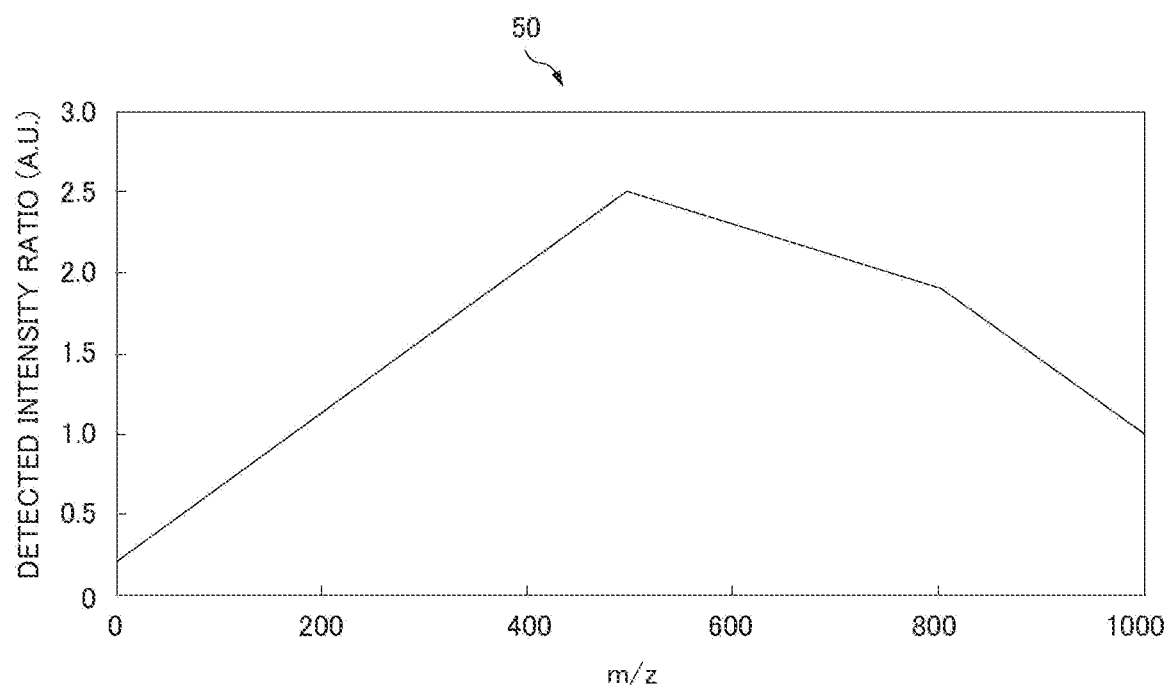
FIG. 7 is a graph showing an intensity ratio due to a difference in sensitivity profile between devices according to a third embodiment of the present invention.

FIG. 7 is a graph 50 showing a difference in the individual difference data of the analyzer 1. The horizontal axis is a mass-to-charge ratio, and the vertical axis is a detected intensity ratio. Here, the individual difference data correspond to an individual difference in which the detection sensitivity to the mass-to-charge ratio is slightly different for each analyzer 1. The sensitivity profile is sensitivity distribution determined based on a common criterion, and a difference in sensitivity profile for each individual is a data variation generated when another analyzer 1 measures the analysis result data on which the simulated data is based. In an example of FIG. 7, when the mass-to-charge ratio is 200 or less, the intensity ratio is smaller than 1.0, and in a range larger than 200, the value of the intensity ratio is larger than 1.0. FIG. 8 shows a mass spectrum 51 of a sample 3 and a mass spectrum 52 obtained by reflecting the difference in the individual difference data of the detection sensitivity of the analyzer 1 in a mass spectrum 51.

As shown in the graph of FIG. 7, in a range in which the mass-to-charge ratio is 200 or less, the value of the intensity ratio is 1.0 or less, and thus the detected intensity of the spectrum of a region 52a of the generated mass spectrum 52 is smaller than the detected intensity of a region 51a of the mass spectrum 51. In a range in which the mass-to-charge ratio is larger than 200, the value of the intensity ratio is larger than 1.0, and thus the detected intensity of a region 52b of the generated mass spectrum 52 is larger than the detected intensity of a region 51b of the mass spectrum 51. The mass spectrum 51 and the mass spectrum 52 are examples of a "plurality of analysis result data" and a "plurality of simulated data" in the claims.

In the analytical data analyzer 300 according to the third embodiment, in a step of generating the simulated data, the mass spectrum 52 is generated by adding the difference in the individual difference data of the analyzer 1 unlike the first embodiment in which the mass spectrum 32 corresponding to the ratio of change of the intensity of the mass spectrum 31 of the sample 3 is generated. In the third embodiment, a plurality of simulated data are generated by adding a variation to the analysis result data (mass spectrum 31) within a range equal to or less than the detected intensity ratio in FIG. 7, and machine learning is performed. In the third embodiment, the same structures as those of the aforementioned first embodiment are denoted by the same reference numerals, and description thereof is omitted.

In the analytical data analyzer 300 according to the third embodiment, in a step of generating the simulated data, the mass spectrum 52 is generated by adding the difference (graph 50) between the individual difference data of the analyzer 1 to the mass spectrum 51 of the sample 3. Then, learning is performed using the generated mass spectrum 52, a discrimination criterion 23b is generated, and discrimination is performed using the generated discrimination criterion 23b.

The remaining structures of the analytical data analyzer 300 according to the third embodiment are similar to those of the analytical data analyzer 100 according to the first embodiment.

(Effects of Third Embodiment)

According to the third embodiment, the following effects are achieved.

According to the third embodiment, as described above, the mass spectrum 52 is generated by adding the difference in the individual difference data of the analyzer 1 to the mass spectrum 51 of the sample 3, learning is performed using the generated mass spectrum 52, and discrimination is performed using the obtained discrimination criterion 23b. Accordingly, learning can be performed using the mass spectrum 52 corresponding to an error of the detection sensitivity of the spectrum between the analyzers 1. Consequently, a decrease in the accuracy of machine learning due to the error of the detection sensitivity between the analyzers 1 can be significantly reduced or prevented.

The remaining effects of the analytical data analyzer 300 according to the third embodiment are similar to those of the analytical data analyzer 100 according to the first embodiment.

[Fourth Embodiment]

The structure of an analytical data analyzer 400 according to a fourth embodiment is now described with reference to FIGS. 1 and 9. In the fourth embodiment, an example in which simulated data is generated by adding a variation caused by a random noise variation that may be mixed at the time of measurement among specific variation factors associated with the measurement is described.

FIG. 9(A) shows a mass spectrum 60 of a sample 3, and FIG. 9(B) shows a mass spectrum 61 obtained by adding a random number to the mass spectrum 60 within a range that does not affect identification. The random number is added, and thus the number of peaks is increased overall in a mass spectrum 61. In the present embodiment, the expression "range that does not affect identification" indicates a range obtained by repeatedly measuring a standard sample based on a range generated in the process of actually collecting data. Furthermore, in the present embodiment, the term "random number" indicates a variation corresponding to a data variation due to random noise that may be inevitably mixed at the time of measurement. The mass spectrum 60 and the mass spectrum 61 are examples of a "plurality of analysis result data" and a "plurality of simulated data" in the claims.

In the analytical data analyzer 400 according to the fourth embodiment, in a step of generating the simulated data, the mass spectrum 61 is generated by adding the random number to the mass spectrum 60 of the sample 3 within the range that does not affect identification unlike the first embodiment in which the mass spectrum 32 corresponding to the ratio of change of the intensity of the mass spectrum 31 of the sample 3 is generated. In the fourth embodiment, the same structures as those of the aforementioned first embodiment are denoted by the same reference numerals, and description thereof is omitted.

The analytical data analyzer 400 according to the fourth embodiment generates the mass spectrum 61 by adding the random number to the mass spectrum 60 within the range that does not affect identification in the step of generating the simulated data. Then, discrimination is performed using a discrimination criterion 23b generated as a result of using the generated mass spectrum 61 for learning.

The remaining structures of the analytical data analyzer 400 according to the fourth embodiment are similar to those of the analytical data analyzer 100 according to the first embodiment.

(Effects of Fourth Embodiment)

According to the fourth embodiment, the following effects are achieved.

According to the fourth embodiment, as described above, in the step of generating the simulated data, the mass spectrum 61 is generated by adding the random number to the mass spectrum 60 within the range that does not affect identification. Accordingly, learning can be performed using the mass spectrum 61 corresponding to the random noise. Consequently, when noise is mixed at the time of measurement, a decrease in the accuracy of machine learning can be significantly reduced or prevented.

The remaining effects of the analytical data analyzer 400 according to the fourth embodiment are similar to those of the analytical data analyzer 100 according to the first embodiment.

[Fifth Embodiment]

The structure of an analytical data analyzer 500 according to a fifth embodiment is now described with reference to FIGS. 1 and 10. In the fifth embodiment, an example in which simulated data is generated by adding a variation caused by an impurity that may be mixed at the time of measurement among specific variation factors associated with the measurement is described.

FIG. 10(A) shows a mass spectrum 70 of a sample 3, and FIG. 10(B) shows a mass spectrum 71 generated by adding the peak of the impurity to the mass spectrum 70. The mass spectrum 70 and the mass spectrum 71 are examples of a "plurality of analysis result data" and a "plurality of simulated data" in the claims.

In the analytical data analyzer 500 according to the fifth embodiment, in a step of generating the simulated data, the simulated data is generated by adding the peak of the impurity to the mass spectrum 70 according to the impurity detected at the time of measurement by the analyzer 1 unlike the first embodiment in which the mass spectrum 32 corresponding to the ratio of change of the intensity of the mass spectrum 31 of the sample 3 is generated. The peak of the impurity not found in a region 70a of the mass spectrum 70 can be confirmed in a region 71a of the mass spectrum 71.

In addition, as the impurity, keratin that has adhered to the finger of an operator, for example, is considered. The impurity that may be mixed is different depending on the sample 3, and thus it is only required to acquire data of the impurity that may be mixed. In the fifth embodiment, the same structures as those of the aforementioned first embodiment are denoted by the same reference numerals, and description thereof is omitted.

In the analytical data analyzer 500 according to the fifth embodiment, in the step of generating the simulated data, the mass spectrum 71 is generated by adding the peak of the impurity to the mass spectrum 70 according to the impurity detected at the time of measurement by the analyzer 1. Discrimination is performed using a discrimination criterion 23b generated as a result of using the generated mass spectrum 71 for learning. In the fifth embodiment, a plurality of simulated data are generated by changing the height of the peak of the impurity, and are used for machine learning.

The remaining structures of the analytical data analyzer 500 according to the fifth embodiment are similar to those of the analytical data analyzer 100 according to the first embodiment.

(Effects of Fifth Embodiment)

According to the fifth embodiment, the following effects are achieved.

According to the fifth embodiment, as described above, the mass spectrum 71 is generated by adding the peak of the impurity to the mass spectrum 70 according to the impurity detected at the time of measurement by the analyzer 1. Accordingly, learning can be performed using the mass spectrum 71 corresponding to the mixing of impurity. Consequently, a decrease in the accuracy of machine learning can be significantly reduced or prevented when the impurity is mixed.

[Sixth Embodiment]

The structure of an analytical data analyzer 600 according to a sixth embodiment is now described with reference to FIG. 11. In the analytical data analyzer 600 according to the sixth embodiment, a data input 7 acquires analysis result data 6 generated by another analyzer, and discrimination is performed using the acquired analysis result data 6 unlike the first embodiment in which discrimination is performed using a mass spectrum 31 generated by an analyzer 1.

Figure 11:
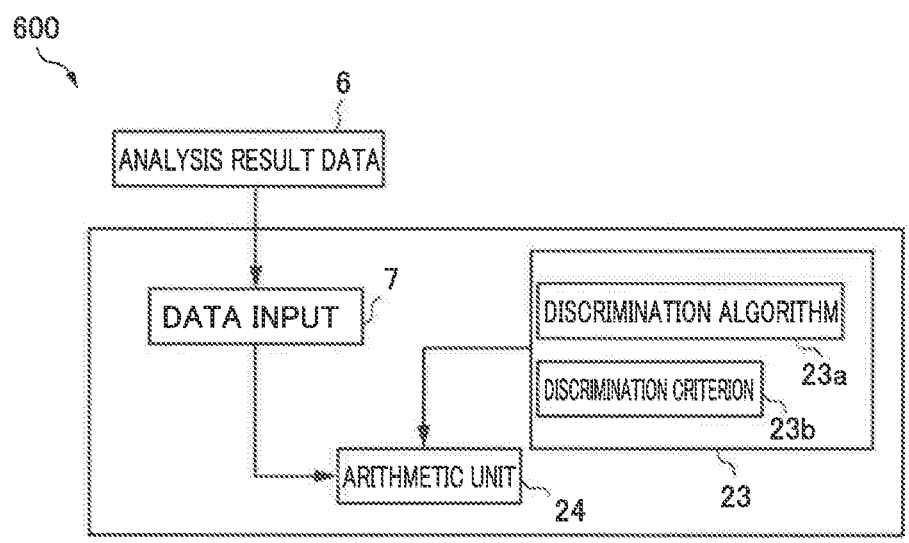
FIG. 11 is a block diagram schematically showing an analytical data analyzer according to a sixth embodiment of the present invention.

As shown in FIG. 11, the analytical data analyzer 600 according to the sixth embodiment includes the data input 7 that acquires the analysis result data 6 generated by another analyzer, a storage 23 that stores a discrimination criterion 23b generated through machine learning using simulated data generated by adding a data variation to the analysis result data 6 within a range that does not affect identification and a discrimination algorithm 23a for machine learning, and an arithmetic unit 24 that discriminates the analysis result data 6 acquired using the discrimination criterion 23b.

The analytical data analyzer 600 according to the sixth embodiment analyzes the analysis result data obtained via an external storage medium such as a hard disk or a USB memory, or the Internet.

(Effects of Sixth Embodiment)

According to the sixth embodiment, the following effects are achieved.

According to the sixth embodiment, as described above, the analytical data analyzer 600 includes the data input 7 that acquires the analysis result data 6, the storage 23 that stores the discrimination criterion 23b generated through machine learning using the simulated data generated by adding the data variation to the analysis result data 6 within the range that does not affect identification and the discrimination algorithm 23a for machine learning, and the arithmetic unit 24 that discriminates the analysis result data 6 acquired using the discrimination criterion 23b. Accordingly, a plurality of simulated data in which the variation has been added within the range that does not affect identification can be generated. Accordingly, the amount of data used for machine learning can be increased, and thus the accuracy of machine learning can be improved.

[Modified Examples]

The embodiments disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the example in which the mass spectrum is obtained as the analysis result data has been shown in each of the aforementioned first to fifth embodiments, the present invention is not restricted to this. Non-spectral data may be used as the analysis result data.

While the example in which the MALDI method is used as the ionization method of the ionizer 10 has been shown in each of the aforementioned first to fifth embodiments, the present invention is not restricted to this. For example, ESI (electrospray method) may be used as the ionization method.

While the example in which the mass spectrometer is provided as the analyzer has been shown in each of the aforementioned first to fifth embodiments, the present invention is not restricted to this. According to the present invention, the spectrum can be obtained as the analysis result data, and any analyzer may be used as long as the same adds a variation associated with the detection to the obtained spectrum. For example, an FT-IR (Fourier Transform Infrared Spectrophotometer) may be used, or a chromatograph may be used.

While the example in which the simulated data in which the variation corresponding to the variation factor generated associated with the measurement has been added is generated, and learning is performed has been shown in each of the aforementioned first to fifth embodiments, the present invention is not restricted to this. According to the present invention, machine learning may be performed by combining the simulated data generated in the first to fifth embodiments, or machine learning may be performed using all the simulated data. According to this structure, the amount of data (the number of data patterns) used for machine learning can be increased, and thus the accuracy of machine learning can be further improved.

While the example in which as a machine learning method, an SVM (support vector machine) is used to generate the discrimination criterion 23b has been shown in each of the aforementioned first to sixth embodiments, the present invention is not restricted to this. For example, a neural network may be used, or AdaBoost may be used. Machine learning using other than these may be performed.

While the example in which the analytical data analyzer 100 is used to discriminate cancer has been shown in the aforementioned first embodiment, the present invention is not restricted to this. For example, the analytical data analyzer may be used to discriminate a disease other than cancer.

DESCRIPTION OF REFERENCE NUMERALS

1: analyzer
6, 31, 40, 51, 60, 70: analysis result data
7: data input
23: storage
23a: discrimination algorithm
23b: discrimination criterion
24: arithmetic unit
30: intensity ratio by mass of sample (specific variation factor associated with measurement by analyzer)
32, 41, 52, 61, 71: simulated data
100, 200, 300, 400, 500, 600: analytical data analyzer

The invention claimed is:

1. An analytical data analysis method using machine learning of a plurality of analysis result data measured by an analyzer, the analytical data analysis method comprising:
generating a plurality of simulated data by adding a data variation to the plurality of analysis result data within a range in which a result of a discrimination of the plurality of analysis result data is not reversed when the data variation is added;
performing the machine learning using the plurality of analysis result data and the plurality of generated simulated data; and
performing discrimination using a discrimination criterion, that is a parameter used for the discrimination obtained through the machine learning, to analyze the plurality of analysis result data.

2. The analytical data analysis method according to claim 1, wherein the range in which the result of the discrimination is not reversed when the data variation is added is a range corresponding to a specific variation factor associated with measurement by the analyzer.

3. The analytical data analysis method according to claim 2, wherein
each of the plurality of analysis result data is a spectrum obtained by the analyzer; and
the specific variation factor is a variation factor caused by the analyzer or a sample and generated when the spectrum is obtained by the analyzer.

4. The analytical data analysis method according to claim 3, wherein the generating of the plurality of simulated data includes generating the plurality of simulated data by varying a value of an intensity of the spectrum according to a ratio of change of the intensity of the spectrum caused by the sample.

5. The analytical data analysis method according to claim 3, wherein the ratio of change of the intensity of the spectrum caused by the sample increases or decreases at a substantially constant rate as a mass of the sample or a wavelength absorbed by the sample increases, and the plurality of simulated data are generated by multiplying the value of the intensity of the spectrum by the ratio of change of the intensity of the spectrum caused by the sample.

6. The analytical data analysis method according to claim 3, wherein the generating of the plurality of simulated data includes generating the plurality of simulated data by giving, to a baseline of the spectrum, a variation corresponding to a variation in the baseline generated at a time of measuring the plurality of analysis result data.

7. The analytical data analysis method according to claim 3, wherein the generating of the plurality of simulated data includes generating the plurality of simulated data by adding a difference in individual difference data of each of a plurality of analyzers.

8. The analytical data analysis method according to claim 3, wherein the generating of the plurality of simulated data includes generating the plurality of simulated data by adding a random number to the plurality of analysis result data within the range that does not affect identification.

9. The analytical data analysis method according to claim 3, wherein the generating of the plurality of simulated data includes generating the plurality of simulated data by adding a peak of an impurity to the spectrum according to the impurity detected at a time of the measurement by the analyzer.

10. The analytical data analysis method according to claim 3, wherein the machine learning is performed, using the plurality of simulated data, on the plurality of analysis result data measured by a mass spectrometer that generates a mass spectrum as the analyzer.

11. The analytical data analysis method according to claim 10, wherein the plurality of analysis result data include the mass spectrum of a biological sample collected from a subject, and the performing of the discrimination includes performing cancer discrimination on the plurality of analysis result data of the sample using the discrimination criterion.

12. The analytical data analysis method according to claim 2, wherein the plurality of simulated data are generated by adding the data variation within a range of variation in the plurality of analysis result data caused by the specific variation factor.

13. The analytical data analysis method according to claim 12, comprising:
  acquiring the variation in the plurality of analysis result data caused by the specific variation factor; and
  generating the plurality of simulated data by adding the acquired variation in the plurality of analysis result data caused by the specific variation factor.

14. An analytical data analyzer comprising:
  a data input that acquires analysis result data obtained by another analyzer;
  a storage that stores a discrimination criterion, that is a parameter used for the discrimination generated through machine learning using simulated data generated by adding a data variation to the analysis result data within a range in which a result of a discrimination of the analysis result data is not reversed when the data variation is added and the analysis result data, and a discrimination algorithm for the machine learning; and
  a processor that discriminates the analysis result data acquired by the data input according to the discrimination algorithm using the discrimination criterion, to analyze the analysis result data.

* * * * *